United States Patent [19]
Watkin et al.

[11] Patent Number: 5,908,388
[45] Date of Patent: Jun. 1, 1999

[54] METHOD AND APPARATUS FOR DETERMINING THE THICKNESS OF BONE IN VIVO

[75] Inventors: Kenneth L. Watkin, Deaconsfield; Lucie Lessard, Verdun; M. Souheil El-Hakim, Montreal; Mohammed M. Elahi, Brampton, all of Canada

[73] Assignee: Martinex R & D Inc., Montréal, Canada

[21] Appl. No.: 08/964,467

[22] Filed: Nov. 4, 1997

[51] Int. Cl.⁶ .................................................. A61B 8/00
[52] U.S. Cl. ............................................................ 600/438
[58] Field of Search ............................... 600/587, 2, 438, 600/439, 442

[56] References Cited

U.S. PATENT DOCUMENTS

5,117,835  6/1992  Mick ......................................... 600/587
5,309,898  5/1994  Kaufman et al. ............................ 601/2

*Primary Examiner*—Marvin M. Lateef
*Assistant Examiner*—Maulin Patel
*Attorney, Agent, or Firm*—Swabey Ogilvy Renault

[57] ABSTRACT

The thickness of bones of the skull is determined in vivo employing ultrasonic waves which are transmitted into the bone; reflected echoes of the transmitted waves are converted into electrical signals and the signals are windowed to identify a zone embracing the bone thickness; a power spectrum is developed of each electrical signal of the windowed zone; the power spectrum is differentiated to provide a plot of frequency and amplitude and the distance between adjacent peaks of the wave plot is measured from which the bone thickness can be computed.

12 Claims, 6 Drawing Sheets

METHOD AND APPARATUS FOR DETERMINING THE THICKNESS OF BONE IN VIVO

BACKGROUND OF THE INVENTION i) Field of the Invention

This invention relates to a method and apparatus for determining the thickness of bones of the skull in vivo.

ii) Description of Prior Art

Cranial bone grafts have become the substrate of choice in rehabilitation and reconstruction of the craniomaxillofacial skeleton; and the calvarium is generally accepted as the best donor site. Advantages of the calvarium as a donor site for bone reconstructive surgery include accessibility, the inherent contour and abundance of harvestable bone, improved graft volume survival and the inconspicuousness of the donor site.

Knowledge of calvarial thickness at the donor site would be of significant assistance to surgeons harvesting calvarial grafts.

Computerized tomography provides a reasonable estimate of cranial thickness, however, this imaging modality lacks precision when extrapolating for in situ assessment.

It has been demonstrated that calvarial bone thickness is subject to regional variation and thus far accurate methods for the in situ or in vivo measurement of skull thickness are not available.

Previously it has been suggested that 6 mm of parietal bone thickness is the threshold for safe in situ calvarial harvesting, while others have suggested that a 2 mm thickness margin of the diploic space should be the limiting factor in obtaining a safe separation plane in split cranial harvests.

Despite the limited number and nature of predictive studies on the assessment of skull thickness, the importance of recognizing the variation between minimum and maximum skull thickness at a particular site is established. This variation can approach 8 mm. The variations and lack of predictability of bone thickness based on tables and charts of average data places predictability well beyond the margin of safety required in the context of consistently harvesting cranial bone without compromising the patient.

Knowledge of the thickness of the maxilla in preparation for cranial facial surgery or dental surgery would also be of value, so as to avoid penetration through the maxilla and potential damage or infection of underlying organs.

Ultrasound has been used in other environments in evaluating thickness or changes in thickness of an industrial article such as result from disintegration or flaking or separation of parts of the article. U.S. Pat. No. 5,351,544 describes a measuring apparatus which employs high frequency ultrasound to determine the thickness and/or flaking state of a specimen along its depth. U.S. Pat. No. 5,440,929 describes an ultrasonic device for measuring thickness of a bottom plate of an oil storage tank. U.S. Pat. No. 3,985,022 describes a technique for ultrasonic measurement of a work piece. U.S. Pat. No. 5,009,103 describes an ultrasonic thickness measuring method and apparatus. U.S. Pat. No. 5,585,563 describes a method for determining the thickness of a specimen such as an optical lens without mechanical contact.

All of these prior methods employing ultrasound are directed to evaluating articles of manufacture where the opposed surfaces of the article are accessible or can be located. None of these prior Patents is concerned with measurement or evaluation of bone or the like, in vivo.

The bones of the skull include the cranium bones and the facial bones, for example, the calvarial and the maxilla.

SUMMARY OF THE INVENTION

It is an object of this invention to provide a method and apparatus for determining the thickness of bones of the skull in vivo.

It is a particular object to provide such a method and apparatus as a preparatory step to harvesting calvarial grafts for use in reconstructive surgery.

It is a further object to provide such a method and apparatus for determining the thickness of the maxilla in preparation for cranial facial surgery or dental surgery.

In accordance with the invention there is provided a method of determining the thickness of bones of the skull in vivo comprising: i) transmitting pulsed ultrasonic waves having a frequency of 1 to 3 MHz into bone, having outer and inner opposed faces, in vivo, in a zone where it is desired to determine thickness of the bone, between the inner and outer opposed faces, ii) receiving the combined echoes of ultrasonic waves reflected at said outer face, and ultrasonic waves transmitted through said bone from said outer face and reflected at said inner face, iii) converting the received echoes from ii) into electrical signals, iv) windowing the electrical signals, v) computing the power spectrum of each windowed electrical signal, vi) differentiating the power spectrum to prove a wave plot of frequency and amplitude, vii) measuring the distance between adjacent peaks of the wave plot, and viii) determining the thickness of the bone between said inner and outer opposed faces of said zone from the distance measured in step vii).

In accordance with another aspect of the invention there is provided an apparatus for determining the thickness of bones of the skull in vivo comprising: a) an ultrasonic transducer for generating pulsed ultrasonic waves having a frequency of 1 to 3 MHz, b) receiving means for receiving reflected echoes of the ultrasonic waves, c) means for converting the reflected echoes into electrical signals, d) window processing means for windowing the electrical signals, e) a spectral analysis unit for developing power spectra of the windowed signals, f) means for differentiating the power spectrum of each signal to provide a wave plot of frequency and amplitude, g) a peak detector unit for determining the distance between peaks of said wave plot, and h) comparator means for calculating the thickness from the distances determined by the peak detector unit in g).

DESCRIPTION OF PREFERRED EMBODIMENTS

The invention may be applied to exposed bone or to bone which has a tissue covering, for example, a covering of skin or mucosa of the oral cavity, depending on the site of the bone under investigation.

In either case it is necessary to determine the zone of the plot of the reflected waves, within which the bone falls. In particular the zone is identified by windowing using a generalized cosine window, for example, a Hamming Window or a Hanning Window. This zone is selected based on known data of bone thicknesses and is selected so as to encompass and extend beyond the bone inner and outer faces.

In the case where the bone is covered by a tissue covering such as skin, account must be taken of the thickness of the skin, in determining the windowed zone embracing the inner and outer faces of the bone. This may be achieved in accordance with the invention by a preliminary step in which pulsed ultrasonic waves having a frequency of 6 to 8 MHz, preferably 7 MHz are transmitted through the tissue covering into the bone; echoes from the tissue surface and the bone outer and inner faces are received and converted into electrical signals. From these signals the thickness of the tissue covering, or in other words, the distance to the bone outer face through the tissue covering is determined and from this is determined the windowing zone for the bone thickness determination.

The distance to the bone outer face through the tissue covering can be determined by a time of flight measurement. More especially, the time of flight from the transducer to the point of reflection from the bone outer face is determined using a peak detection until which identifies peaks in the electrical signal derived from the reflected echoes to identify the bone outer face and the tissue surface.

In connection with this latter embodiment of the invention the apparatus further includes an ultrasonic transducer for generating pulsed ultrasonic waves having a frequency of 6 to 8 MHz. This may be a transducer separate from the transducer employed to generate the pulsed ultrasonic waves having a frequency of 1 to 3 MHz; or a transducer may be employed which has an adjustment or control enabling shift between the two classes of pulsed ultrasonic wave required in this embodiment of the invention.

In the differentiated power spectrum employed to determine the bone thickness, the distance between adjacent peaks of the wave plot is measured. This measurement may be of the distance between adjacent negative peaks, or the distance between adjacent positive peaks. More especially the distance between adjacent major peaks is employed.

DESCRIPTION OF PREFERRED EMBODIMENTS WITH REFERENCE TO THE DRAWINGS

Figure 1:
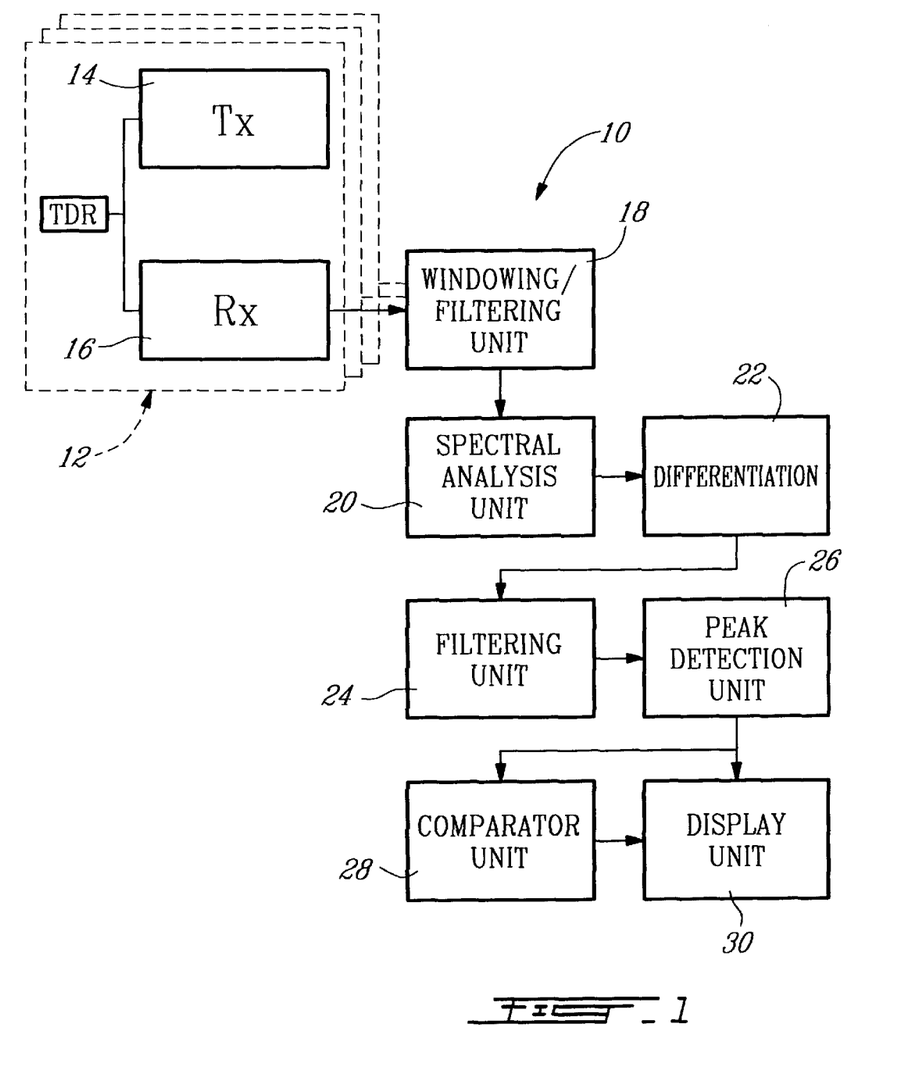
FIG. 1 illustrates schematically an apparatus of the invention for carrying out the method of the invention.
Figure 2:
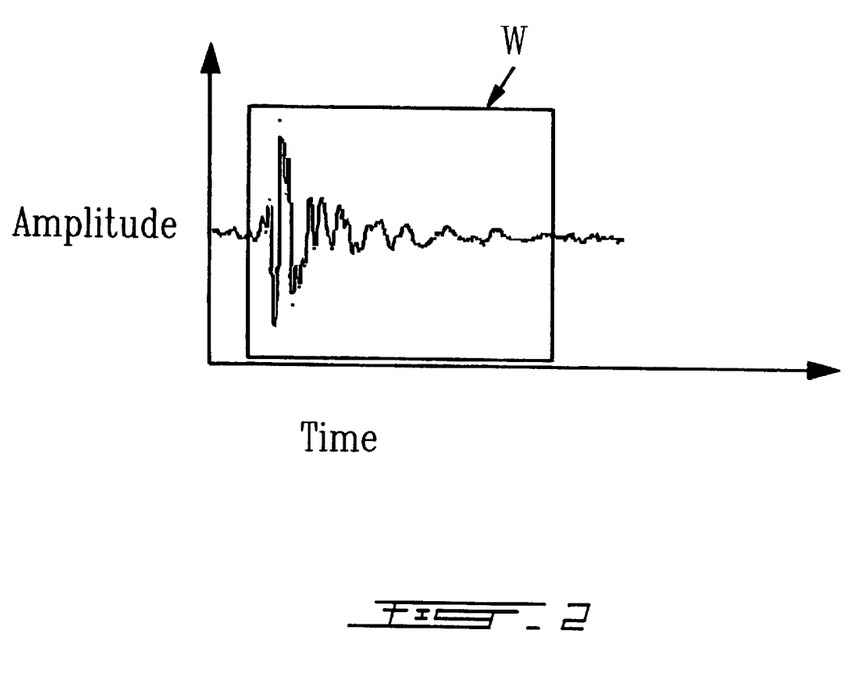
FIG. 2 shows a windowed original wave signal plot of amplitude with time.

With further reference to FIG. 1, an apparatus 10 schematically illustrated includes one or more ultrasonic transducers (TDR) 12 each having a transmitter (TX) 14 and a receiver (RX) 16. The dotted lines indicate one or a plurality of transducers 10.

Receiver 16 communicates with a windowing/filtering unit 18 which communicates with a spectral analysis unit 20 which communicates with a power spectrum computing station 22.

Computing station 22 communicates with a filtering unit 24 which communicates with a peak detection unit 26.

Peak detection unit 26 communicates with a comparator unit 28 and with a display unit 30. Comparator unit 28 also communicates with display unit 30.

In operation, the apparatus 10 provides a numerical value for bone thickness based upon the signals received by receiver 16 from transmitter 14 of the transducer 12.

The invention is further described by reference to the method as applied to measurement of the thickness of cranium bone, in vivo.

The transducer 12 suitably with a stand-off medium is placed against an exposed clean area of the cranium bone which is a potential site for bone harvesting; low frequency ultrasound waves of 1 to 3, preferably about 2 MHz are generated by transducer 12.

Some of the ultrasound waves are reflected by the outer exposed surface of the cranium bone and some are transmitted through the bone and are reflected at the concealed inner face of the cranium bone opposed to the outer exposed face. The combined reflected waves produce an echo signal which is received by receiver 16.

A standoff medium such as an aqueous gel may be disposed between the transmitter 14 and the outer exposed surface of the cranium bone.

A stand off medium is an acoustically transparent medium, for example, water or a water-soluble gel, which provides a separating distance between the transmitter 14 and the clean surface.

Receiver 16 converts the echoes into an electrical signal which signal may be amplified and stored in a memory (not shown) for future processing by the windowing/filtering unit 18 or may be fed directly for processing by the windowing/filtering unit 18.

In unit 18 the electrical signal from receiver 16 or from memory storage is processed or windowed using a generalized cosine window (e.g., Hamming Window or Hanning Window) for a region that embraces the bone thickness region. This is illustrated in FIG. 1 which shows the electrical signal from receiver 16 and a windowed zone W. The data within window zone W are used for subsequent processing.

Thus the windowed zone W is a zone which bounds the outer and inner faces of the bone; thus the extremities of the windowed zone are beyond the outer and inner faces of the bone, respectively.

Figure 3:
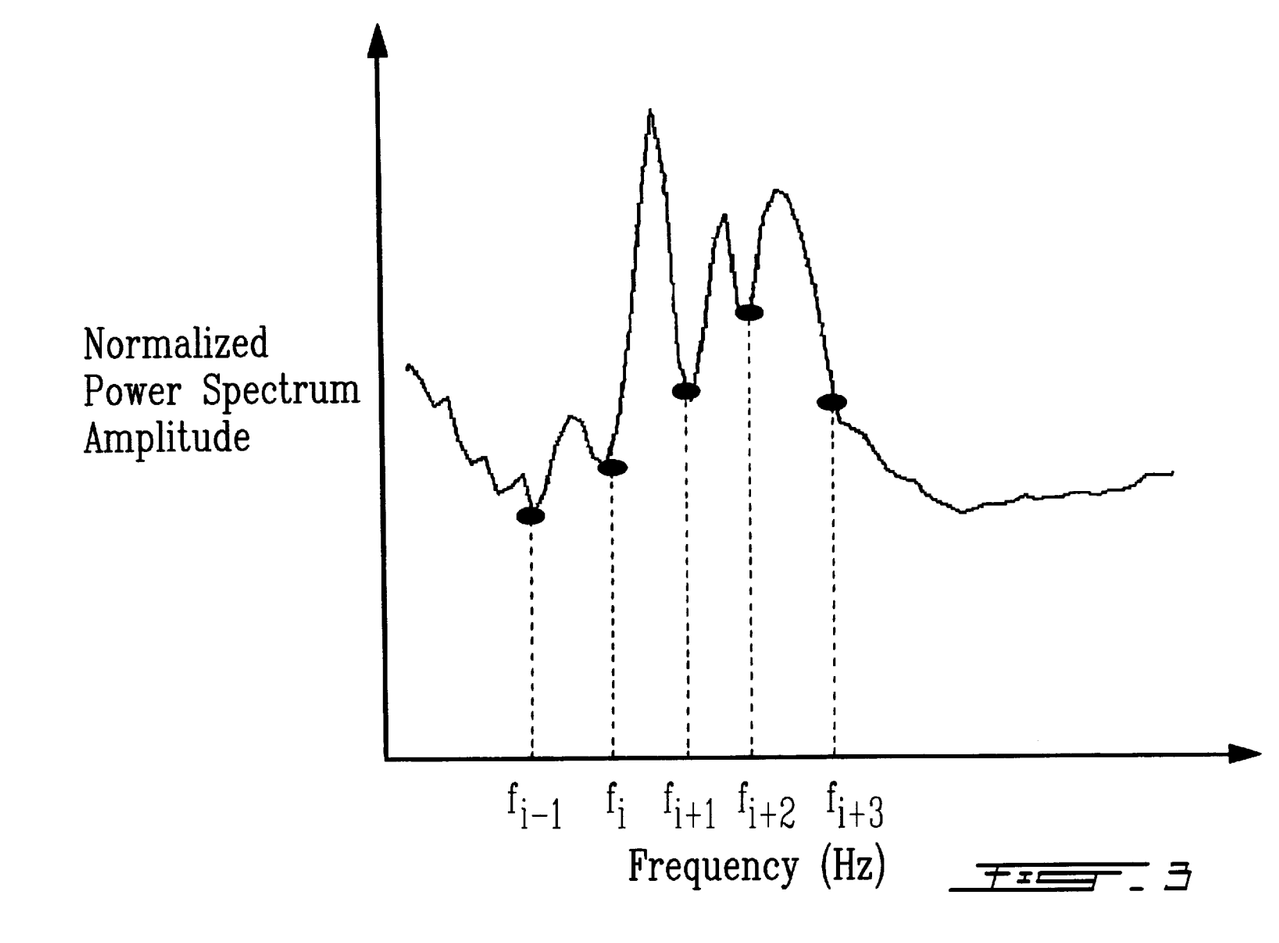
FIG. 3 shows a power spectrum plot of amplitude against frequency derived from the window of FIG. 2.

The unit 18 filters the data of the windowed zone W, typically with a bandpass filter having a filter range from 10,000 to 2,000,000 Hertz. This filtering removes electronic background noise having a frequency above 2 MHz and below 10,000 Hz. The filtered signal is processed in spectral analysis unit 20 to produce a normalized power density spectrum as illustrated schematically in FIG. 3. This shows the signal in the form of a plot of amplitude against frequency of the echoed waves.

Figure 4:
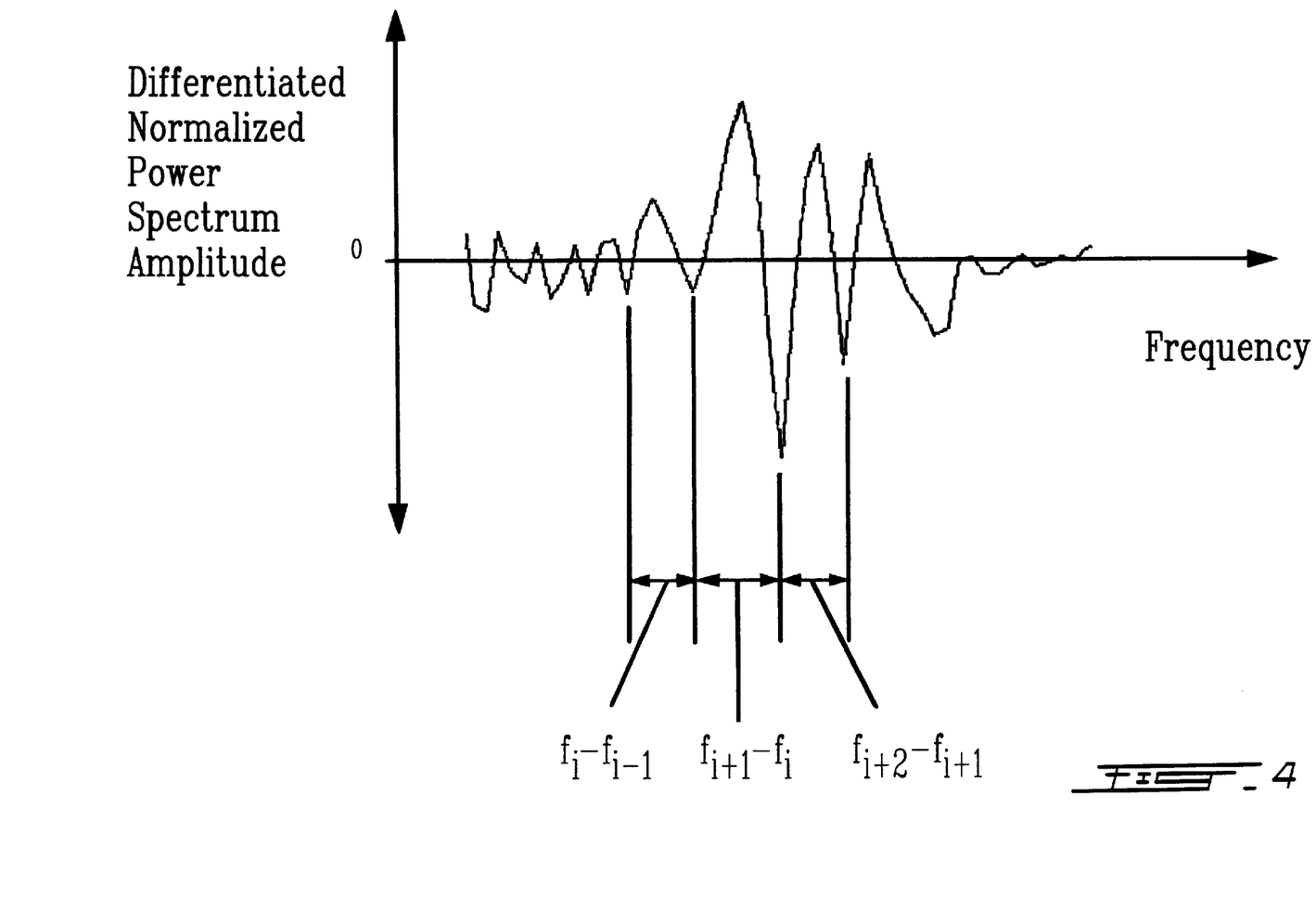
FIG. 4 shows a differentiated power spectrum derived from the plot of FIG. 3.

The normalized power density spectrum is differentiated at power spectrum computing station 22 to provide a differentiated amplitude by frequency display. The signal from station 22 is optionally filtered, typically with a low pass filter to smooth out the signal by removing electronic background noise and the output is processed in a peak detection unit 26, which determines the distance between adjacent major negative peaks $f_i - f_{i-1}$, $f_{i+1} - f_i$, $f_{i+2} - f_{i+1}$ etc., as illustrated in FIG. 4, the frequency $f_{i-1}$, $f_i$, $f_{i+1}$, $f_{i+2}$, $f_{i+3}$, etc. at each sequential negative peak is also determined corresponding to each of $f_{i-1}$, $f_i$, etc.

The thickness D of the cranium skull is determined by comparator unit 28 in accordance with equation I:

$$D = V/2(f_{i+1} - f_i) \qquad \qquad \text{I}$$

where

V is the estimated average velocity of sound in bone, $f_i$ and $f_{i+1}$ identify frequencies of any two adjacent negative peaks $f_{i-1}$, $f_i$, etc.

The thickness D may be calculated in comparator unit 28 using a single pair of adjacent frequencies $f_{i-1}$, fit $f_{i+1}$, etc. or as an average based on multiple pairs of adjacent frequencies, for example, $f_{i-1}$ and $f_i$; $f_i$ and $f_{i+1}$; $f_{i-1}$ and $f_{i+3}$, etc.

The method can be carried out in a like manner in which peak detection unit 26 determines the distance between adjacent major peaks, with the frequency at each sequential positive peak being determined corresponding to each of the major positive peaks, instead of the major negative peaks.

Verification of the accuracy of the method of the invention was carried out employing a porcine skull and comparing the thickness determined by the method of the invention with the thickness determined by digital calipers. In each case the average of 10 measurements was employed. The average thickness of the skull achieved with the method of the invention was 2.96 mm whereas the average achieved with the digital caliper at the same location was 3.11 mm, a difference of only 0.15 mm.

Figure 5:
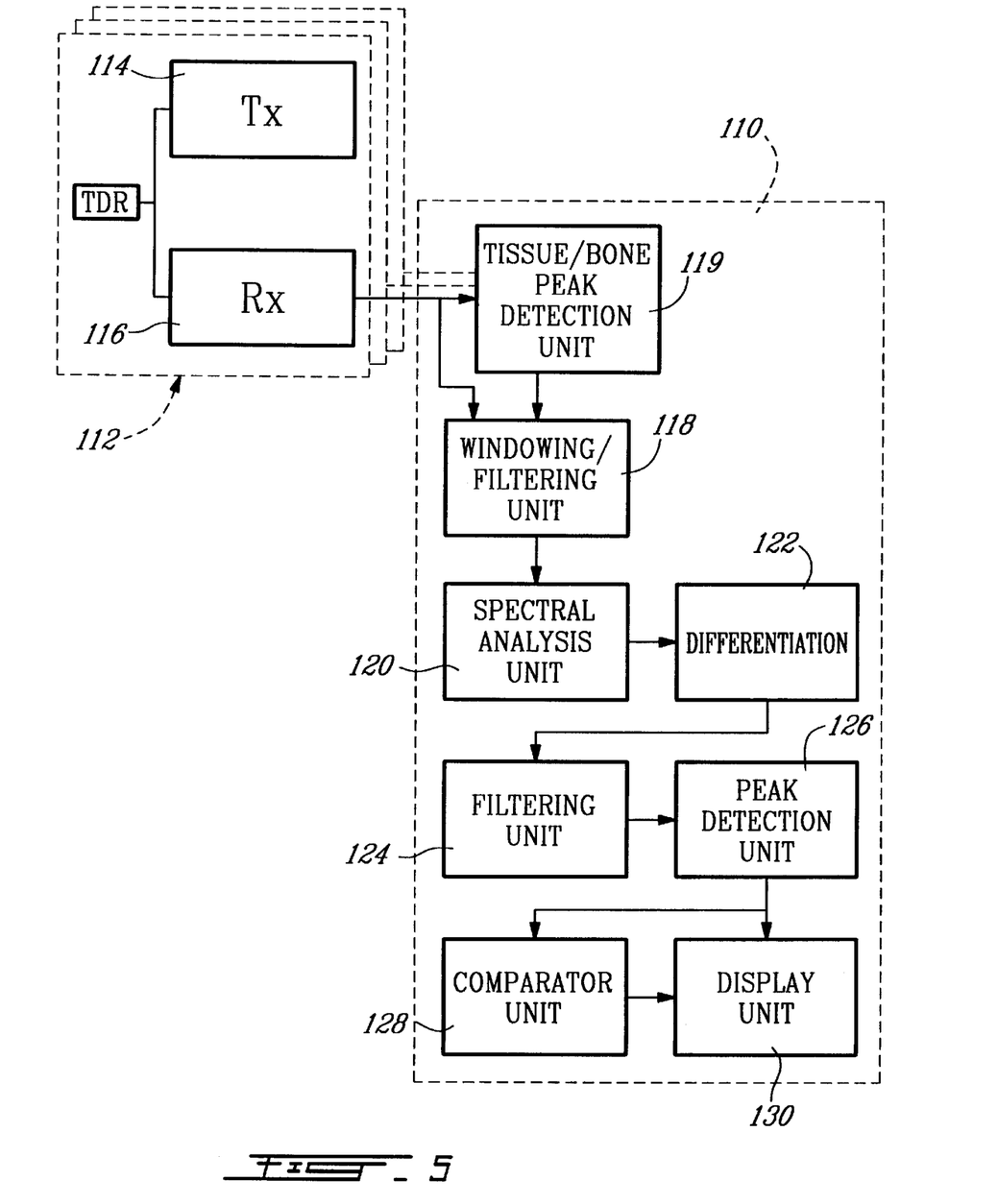
FIG. 5 illustrates schematically an apparatus of the invention in a different embodiment.

With further reference to FIG. 5 there is shown a variation of the apparatus of FIG. 1. The apparatus 10 of FIG. 1 is employed in an embodiment in which the transducer 12 is placed against exposed bone, with or without a stand off medium, to determine the thickness of the bone.

In a second embodiment, employing an apparatus such as is illustrated schematically in FIG. 5, the bone thickness measurement is conducted through the overlying skin surface or other surface such as the mucosa of the oral cavity.

With reference to FIG. 5 the components having the same function as in FIG. 1 are identified by the same integers as in FIG. 1, raised by 100. Thus FIG. 1 shows an apparatus 110 having one or more transducers 112 each having a transmitter 114 and a receiver 116.

It will be seem that the apparatus 110 of FIG. 5 differs from the apparatus 10 of FIG. 1 in the inclusion of a tissue/bone peak detection unit 119.

With reference to the embodiment of FIG. 5, the thickness of the skin or the distance of the bone from the transducer 112 is determined in order to identify the precise region of the windowing unit 118 and for the subsequent bone thickness measurement. Typically a 6–8 MHz sampling range is used with a preferred value of 7 MHz. Given the velocity of sound in biological tissue, 1540 m/sec., the wavelength of a 7 MHz ultrasound wave is approximately 2.2e–4 m. Thus, in a 1 mm thick sample of skin on top of a bone approximately four ultrasonic oscillations would occur before the entering ultrasonic wave would be reflected from the bone. This gives rise to both an entering reflection from the skin surface and a reflection from the bone surface.

Figure 6:
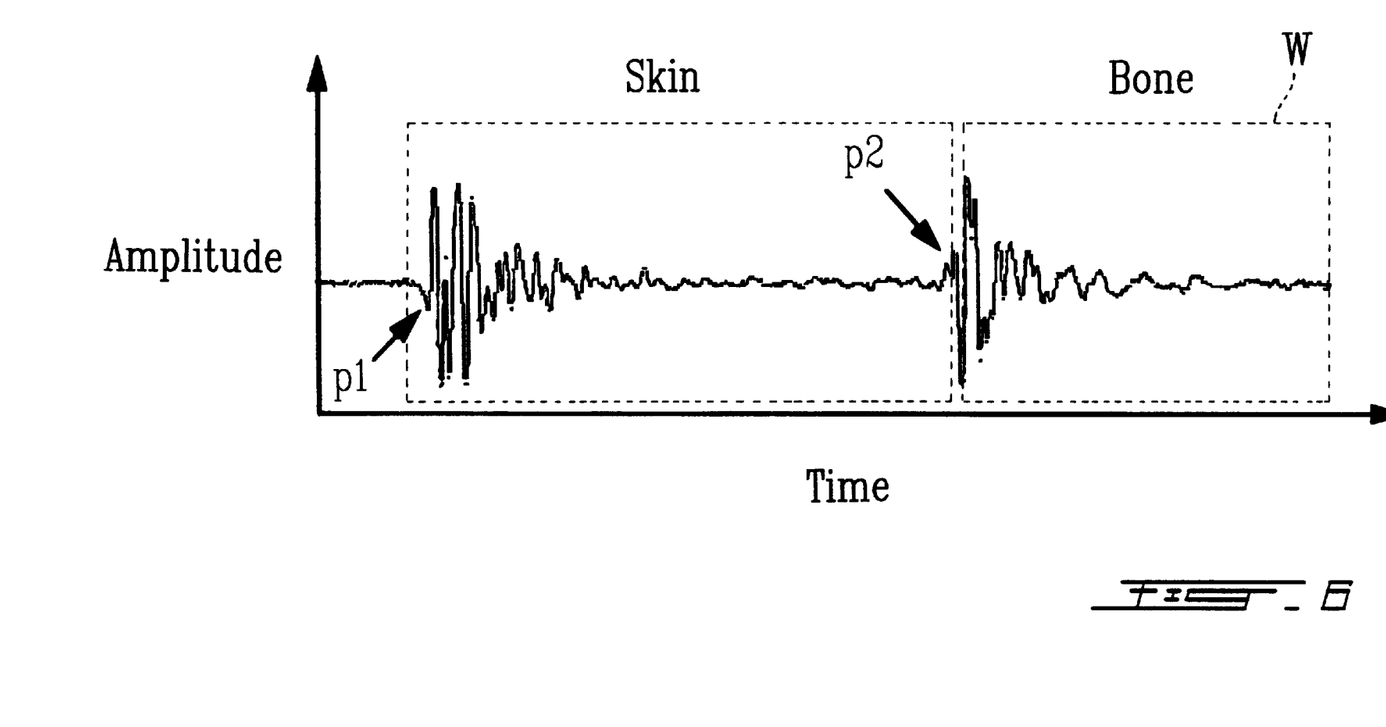
FIG. 6 shows a windowed wave signal plot of amplitude with time for the apparatus of FIG. 5.

An example of these reflections appears in FIG. 6. The distances from the transducers 112 to the bone through the skin can be determined using a time-of-flight measurement. The time-of-flight from the transducers 112 to the reflection from the bone surface is determined using peak detection unit 119. The detected peaks (see FIG. 6) p1 (surface) and p2 (bone) are then used to determine the starting point for the windowing unit 118.

The windowed zone is identified as W, in FIG. 6, and it is this zone W which is filtered in unit 118. The procedure described with reference to FIG. 1 is thereafter followed employing the windowed zone W developed as in FIG. 6.

EXAMPLE

In vivo validation of the ultrasonic thickness method of the invention was conducted using a live Landrace pig (25 kg+/−2 kg). This animal was made available prior to euthanasia for the primary experimental purpose to study the effects of hepatic xenografts. It has been previously sedated with an intramuscular injection of diazepam (2 mg/kg) and anesthetized with inhalation of isofluorane 1–2%, mixed with 95% oxygen and 5% carbon dioxide. Intravenous sodium pentobarbital and prophylactic ibeprenorphine were administered to ensure appropriate anesthesia and analgesia, respectively.

The scalp of the pig was incised and retracted to the level of the suborbital rims bilaterally. A periosteal elevator ensured removal of a remaining soft tissue overlying the calvarium. The point chosen for sampling was chosen to reflect the variability in thickness of the porcine skull and permanently marked for later caliper measurement.

Thickness of the porcine skull was determined using two different techniques—direct digital caliper measurements and ultrasonic thickness measurement using the methods described above. Ultrasonic measurements were performed first.

Ultrasonic measurements were performed using a Matec (model SR9000 [Matec Corporation, Nautick, Mass., U.S.A.]) microcomputer based pulser/receiver. A single crystal (1.27 cm diameter) unfocussed, broadband transducer was attached to the pulser/receiver. The center frequency of the transducer was 1.0 MHz. with a 6dB bandwidth of 1.84 MHz. The transducer was placed on an acoustic standoff device. This device was a cylindrical tube containing de-ionized water. The output of the pulser/receiver was digitized at a sampling rate of 25 MHz using a Tecktronix (model TDS 250) digital oscilloscope whose output was connected to the GPIB bus (IEEE 448) of the microcomputer. Ten (10) samples were stores on the microcomputer hard disk. These digital samples were then windowed using a generalized cosine window and filtered using a bandpass from 10 kHz to 2.0 MHz. The power density spectrum was calculated for the windowed region; see FIG. 3. Power density spectrum minima are identified as $f_{i-1}$, $f_i$, $f_{i+1}$, $f_{i+2}$, $f_{i+3}$. The stores power density spectrum was then differentiated and plotted in spectral format; see FIG. 4. The negative peaks were then detected, see $f_i - f_{i-1}$, $f_{i+1} - f_i$, $f_{i+2} - f_{i+1}$ in FIG. 4. These peaks were used to determine the thickness of the bone sample using formula (I) above.

$f_i - f_{i-1}$ = 543,000 Hz D=3.00 mm $f_{i+1} - f_i$ = 555,000 Hz D=2.93 mm $f_{i+2} - f_{i+1}$ = 551,000 Hz D=2.95 mm

After completion of the ultrasonic measurements a full thickness bone wedge was created using a sagittal saw. The bone segment underwent calvarial thickness measurement at the same marked points used for the ultrasound measurements. A digital caliper, Mitutoyo (model 500 [Mitutoyo Limited, London, UK]) with a resolution of 0.01 mm was utilized to make 4 measurements at the marked point.

RESULTS

The average of the 4 caliper measurements of the wedge bone samples was 3.11 mm while the average for the 10 ultrasound samples was 2.96. The difference between the two measurements was 0.16 mm.

We claim:

1. A method of determining the thickness of bones of the skull in vivo comprising:

i) transmitting pulsed ultrasonic waves having a frequency of 1 to 3 MHz into bone, having outer and inner opposed faces, in vivo, in a zone where it is desired to determine thickness of the bone, between the inner and outer opposed faces, ii) receiving the combined echoes of ultrasonic waves reflected at said outer face, and ultrasonic waves transmitted through said bone from said outer face and reflected at said inner face, iii) converting the received echoes from ii) into electrical signals, iv) windowing the electrical signals, v) computing the power spectrum of each windowed electrical signal, vi) differentiating the power spectrum to provide a wave plot of frequency and amplitude, vii) measuring the distance between adjacent peaks of the wave plot, and viii) determining the thickness of the bone between said inner and outer opposed faces of said zone from the distance measured in step vii).

2. A method according to claim 1, wherein said pulsed ultrasonic waves in i) have a frequency of about 2 MHz.

3. A method according to claim 2, wherein step iv) comprises processing the electrical signals with a generalized cosine window.

4. A method according to claim 1, wherein the windowed signals from step iv) are filtered at a filter range of 10,000 to 2,000,000 Hertz prior to step v).

5. A method according to claim 4, wherein a signal corresponding to the wave plot of step vi) is filtered prior to step vii).

6. A method according to claim 1, wherein said measuring in step vii) is of the distance between adjacent negative peaks of the wave plot.

7. A method according to claim 1, wherein said measuring in step vii) is of the distance between adjacent positive peaks of the wave plot.

8. A method according to claim 1, wherein in step i) said bone is exposed and said pulsed ultrasonic waves are transmitted into said exposed bone.

9. A method according to claim 1, wherein in step i) said bone has a tissue covering and including a step prior to step i) of transmitting pulsed ultrasonic waves having a frequency of 6 to 8 $MHO_z$ through said tissue covering into the bone, receiving echoes from the tissue surface and from the bone outer and inner faces, converting the echoes into electrical signals, determining the distance to the bone outer face through the tissue covering therefrom, and determining therefrom a window zone from step iv).

10. Apparatus for determining the thickness of bones of the skull in vivo comprising:

a) an ultrasonic transducer for generating pulsed ultrasonic waves having a frequency of 1 to 3 MHz, b) receiving means for receiving reflected echoes of the ultrasonic waves, c) means for converting the reflected echoes into electrical signals, d) window processing means for windowing the electrical signals, e) a spectral analysis unit for developing power spectra of the windowed signals, f) means for differentiating the power spectrum of each signal to provide a wave plot of frequency and amplitude, g) a peak detector unit for determining the distance between peaks of said wave plot, and h) compactor means for calculating the thickness from the distance determined by the peak detector unit in g).

11. Apparatus according to claim 10, further including:

i) an ultrasonic transducer for generating pulsed ultrasonic waves having a frequency of 6 to 8 MHz for transmission into a tissue covering and bone;

j) receiving means for receiving reflected echoes of the ultrasonic waves, k) means for converting the reflected echoes into electrical signals, and l) a peak detection unit for identifying peaks defining boundaries of said tissue covering from which a zone for windowing in d) is determined.

12. Apparatus according to claim 10, wherein said window processing means is generalized cosine windowing means.

* * * * *